United States Patent [19]

Shaw

[11] Patent Number: 5,385,551
[45] Date of Patent: Jan. 31, 1995

[54] NONREUSABLE MEDICAL DEVICE WITH FRONT RETRACTION

[76] Inventor: Thomas J. Shaw, 1510 Hillcrest, Little Elm, Tex. 75068

[21] Appl. No.: 125,292

[22] Filed: Sep. 22, 1993

[51] Int. Cl.⁶ .............................................. A61M 5/00
[52] U.S. Cl. ..................................... 604/110; 604/195
[58] Field of Search .............. 604/110, 195, 187, 198, 604/218; 128/763–765

[56] References Cited

U.S. PATENT DOCUMENTS

| | | | |
|---|---|---|---|
| 3,306,290 | 2/1967 | Weltman . | |
| 4,747,831 | 5/1988 | Kulli | 604/110 |
| 4,838,863 | 6/1989 | Allard et al. | 604/110 |
| 4,838,869 | 6/1989 | Allard | 604/195 |
| 4,841,985 | 6/1989 | Wanamaker | 128/763 |
| 4,874,382 | 10/1989 | Lindemann et al. | 604/195 |
| 4,904,242 | 2/1990 | Kulli | 604/110 |
| 4,955,870 | 9/1990 | Ridderheim et al. | 604/195 |
| 4,994,034 | 2/1991 | Botich et al. | 604/110 |
| 5,019,044 | 5/1991 | Tsao | 604/110 |
| 5,046,508 | 9/1991 | Weissler | 128/763 |
| 5,049,133 | 9/1991 | Pascual | 604/110 |
| 5,053,010 | 10/1991 | McGary et al. | 604/110 |
| 5,064,419 | 11/1991 | Gaarde | 604/195 |
| 5,084,029 | 1/1992 | Tagliaferri et al. | 604/195 |
| 5,092,853 | 3/1992 | Couvertier, II | 604/195 |
| 5,114,410 | 5/1992 | Batlle | 604/195 |
| 5,120,310 | 6/1992 | Shaw | 604/110 |
| 5,188,599 | 2/1993 | Botich et al. | 604/110 |
| 5,201,710 | 4/1993 | Caselli | 604/110 |

FOREIGN PATENT DOCUMENTS

146773  9/1990  Japan .

*Primary Examiner*—John D. Yasko
*Attorney, Agent, or Firm*—Harris, Tucker & Hardin

[57] ABSTRACT

A nonreusable medical device has a needle for injecting or collecting fluid which is retractable by depression of a plunger slidingly mounted in the medical device. A front-mounted retraction mechanism has a needle holder connected to the needle. The needle holder is supported along the axis of the device by means of a frictionally engaged retainer ring member coupled to the needle holder along an axially aligned sliding interface. The needle holder and retainer ring are positioned in the front portion of a hollow body. The front of a movable member or plunger presses against the retainer member passing around the needle holder which cannot move forward, thereby separating the retainer member from the needle holder. The separation occurs by gradually reducing the extent of the sliding interface area until the retainer member pops loose from the needle holder whereupon the needle holder and needle are retracted into a cavity in the plunger in response to a retraction force applied to the needle holder by a previously compressed spring.

33 Claims, 4 Drawing Sheets

NONREUSABLE MEDICAL DEVICE WITH FRONT RETRACTION

BACKGROUND OF THE INVENTION

1. Field of the Invention

This invention relates to a medical device, and more particularly, to a non-reusable syringe having an automatically retracting hypodermic needle which renders the syringe non-reusable after one use.

2. Background of the Art

Intravenous drug users have been identified as major vectors for the spread of AIDS in the general population because of sharing and reuse of hypodermic needles. With no vaccine in sight and reeducation lengthy and ineffective, a technological solution to discourage needle reuse is imperative. An additional consideration is that IV drug users obtain syringes primarily from the medical industry. Therefore, any device that reaches the drug-using community would also have to achieve acceptance in the health care field. The primary concerns of the health care industry are that new syringes 1) maintain the same capacity to hold fluids and allow for accurate incremental measurement of fluid as compared with standard syringes; 2) permit one-handed use so that the other hand of the health care worker is free to assist in holding the patient; 3) retract fully after use, thereby eliminating the possibility of needle sticks because of a mistaken belief the syringe has retracted fully when, in fact, it has not; 4) can clearly indicate prior use; 5) be extremely reliable even when used at a wide range temperature; 6) be easily assembled for mass production, and 7) be manufactured at an extremely low cost, due to the daily consumption of the product in quantities of millions of individual syringes, while maintaining a zero defect failure rate.

Various syringes with retracting or disarming technology have been devised in an attempt to address the needs of the health care industry. A number of different approaches have been used.

U.S. Pat. No. 4,747,831 to Kulli discloses a syringe-like cannula insertion set with a retraction needle. A manually releasable latch requires two-handed operation to release the needle after use. An IV drug user may simply not activate the manual release. Another example of a manually releasable needle in a safety syringe is U.S. Pat. No. 4,874,382 to Lindemann, et at., which also demonstrates the use of a "silo" to contain a retraction spring. The silo desirably protects the fluid from contact with the spring, but occupies volume which tends to undesirably increase the size of the syringe.

U.S. Pat. No. 5,064,419 to Gaarde combines a front-mounted retraction spring held against a yielding wall which must be flexed out of the way by the end of the plunger to allow retraction. Discrepancies in thickness or elasticity of the yielding wall can lead to release problems. Hang-ups can occur if the retraction spring catches the edge of the yielding wall during release. The device lacks a positive seal to prevent contact between fluid and spring. The seal depends upon pressure from the retraction spring and the quality of surfaces at the opening in the yielding wall.

U.S. Pat. No. 4,838,869 to Allard depends on flexing or breaking of clamps which are molded into the syringe or another part secured in the syringe and broken by the plunger. It also discloses a diaphragm in the plunger which must be penetrated by the needle and spring. These structures present serious quality control and assembly problems. Small broken off pieces can present a risk of hang-ups.

U.S. Pat. No. 4,994,034 to Botich, et at., illustrates a needle holder held by hooks in the front of the syringe and a frangible member molded across the front opening of the plunger, which has angled edges to spread the hooks. The hooks are molded as part of a front housing through which the needle passes. The housing is sealed to the syringe body with an "O" ring between the housing and syringe body. The fluid medication is free to contact the spring and spring holder. Outward lateral spreading of the hooked fingers is required to release the needle holder. The required flexing of the resilient fingers and hooks limit choice of materials and molding processes to achieve the right degree of elasticity without requiring excessive force to initiate retraction. Non-uniform flexing or breaking could lead to hang-ups. It is believed that molding the hooked housing would require molding with the aid of a collapsible core pin. Collapsible core technology tremendously increases mold cycle time, thus driving costs upward. The frangible piece on the end of the plunger must break readily and cleanly during retraction. Any jagged edges could catch the spring, causing jams. The degree of brittleness of the plunger material and dimensional control would make reliability difficult to obtain. A special seal for the needle is required at the tip to keep from drawing air into the fluid chamber and to prevent leakage.

U.S. Pat. No. 5,084,029 to Tagliaferri, et al., illustrates another approach using a frangible membrane on the plunger and a needle holder which can be hooked by a male hooking pawl which is held in the barrel by small shearing pins. The pins must shear upon application of sufficient force after hooking to allow the needle assembly to be withdrawn from the end of the syringe.

U.S. Pat. No. 5,053,010 to McGary, et al., is another example of a front-mounted retraction device which relies upon molding of structures which break or shear in order to provide a release. The front of the plunger shears through the piston, then breaks off part of the syringe body to release a spring-loaded needle holder. This creates obvious reliability problems in molding a body that will hold the compressed spring, yet break consistently without excessive effort. This device illustrates another potential problem in that failure of the syringe to fully penetrate through the head of the piston, yet breaking the needle-holding parts, could result in driving the needle forward into the patient's body at the moment of intended retraction.

The above-mentioned art illustrates the many attempts to produce a practical automatically retractable non-reusable syringe. The most commonly used syringes are 1 cc and 3 cc syringes which must be mass-produced at the rate of millions per day. The tiny needles are produced in the form of coiled tubing, and vary significantly from absolute straightness after they are cut to length. This alone leads to difficult assembly problems if the needle must be passed through a small opening. The extremely sharp tip of the needle will catch the edge of a hole and jam the production line. Any hope of high-speed production requires molds with 64 cavities or more to reduce unit cycle time. Therefore, molded structure within the barrel that requiring collapsing core pins such as are shown in some of the art mentioned are unlikely to be producible at competitive costs.

The gravity of the threat posed by AIDS and the fact that the main vector of the spread of the dreaded disease is through reuse of syringes by IV drug users has resulted in intense activity to develop the most practical, most reliable, easily assemblable, mass-producible syringe. A study of the problem reveals at least ten features that a retractable syringe should address in order to be a marketable product in quantities that could impact the spread of AIDS. A failure to address any one of these items could and has prevented the production of a practical retractable syringe. Such a syringe should:

1. Require only one inner contraction in the barrel so as to be formed by the separation of core pins at the kiss off point without the use of collapsible core technology. If collapsible core technology is required, the product can Be rendered noncompetitive due to production costs as a result of excessive cycle time.

2. The device should have a mechanism to prevent accidental retraction when the plunger is pushed all the way forward prior to drawing medications. This helps prevent accidental firing of the retraction mechanism. Syringes that accidentally "fire" and become useless during medical emergencies will never become accepted in the medical community.

3. Once the needle has been retracted, the device should be very difficult or impossible to reuse or reassemble for reuse.

4. The release mechanism should not require bending, flexing, or breaking of any release elements if the force applied by the thumb to initiate retraction is to be constant under various climatic conditions. Designs requiring breakage of parts for release create manufacturing and reliability problems when trying to achieve a very thin breakable membrane.

5. The needle must not advance even slightly forward at the retraction moment, for to do so drives it painfully into the patient.

6. The design must provide for easy assembly methods which do not require guiding the needle into small holes because presently manufactured needles, when epoxied into hubs or needle holders, are not perfectly aligned.

7. The design should not call for the use of minute parts that are delicate and drive up assembly costs while hampering reliability by increasing the risk of hang-ups during retraction.

8. The seals should be sufficient to prevent liquid leakage but must also prevent loss of vacuum. The biasing spring should be effectively sealed from the variable liquid holding chamber.

9. The amount of force required to initiate retraction should be predeterminable and not affected by creep of plastics or require the use of special plastic compositions.

10. The device should not be reusable if the plunger is sufficiently extended during the prior use to cause a retraction.

It would therefore be desirable to produce a practical syringe that meets these requirements. The syringe disclosed herein is the first mass-producible syringe suitable for use in a small size which meets all these requirements.

SUMMARY OF THE INVENTION

A medical device is disclosed having a retraction mechanism equipped with a needle for injecting or collecting fluid which operates on a new principle. The device is primarily useful in the syringe technology where front-mounted retraction mechanisms are employed. It can also be adapted for use as a blood sampling device by providing the usual double-ended needle and replacing the plunger with a collecting tube equipped with a rubber stopper adapted to operate the retraction mechanism.

The retraction mechanism comprises a needle holding member which is surrounded by a retainer member, the needle holding member and retainer member being separable members coupled, along a sliding interface oriented in the direction of retraction, with a friction force which exceeds the retraction force. The direction of retraction is substantially parallel to the longitudinal axis of the device, such as a syringe, or only slightly angled from the axis to facilitate reproducible and reliable assembly of the retainer member to the needle holding member.

The needle holding member and retainer coupled at the sliding interface, are mounted in the front end portion of an elongate hollow body containing a movable member such as a syringe plunger. The needle holding member, together with a hollow needle fixed therethrough, are mounted in the center of the hollow end portion with the needle extending along the central axis of the device. The needle holder, but not the retainer member, is restrained from forward movement by a closure member mounted at the front tip of the hollow front portion. The closure member does not also restrain the retraction member.

Retraction is initiated by relative movement between the needle holding member and the retainer member caused by selective movement of the movable member toward the front of the device. Retraction occurs by reduction of the extent of the sliding interface in response to movement of the movable member, until the retraction force exceeds the friction force, whereby the needle holding member separates from the release element by moving forward, allowing the needle holder and needle to move into the retracted position under the influence of the biasing element.

More particularly, an elongate hollow body has a hollow first end portion separated by a transition zone from a second hollow end portion. Substantially all of the retraction mechanism is located within the first end portion of the body below the transition zone. The transition zone includes a stop member against which the retainer member is positioned prior to retraction. The retainer member is smaller in height than the needle holding member such that the retainer member is free to move axially when urged to move in that direction by the movable member, while the needle holding member is fixed in position by being bottomed out against the closure member at the tip. A biasing element, preferably a spring, applies a retraction force to the needle holding member tending to push it rearwardly into the hollow body. The needle holding member is preferably cylindrically T-shaped, having a stem portion serving as a guide for the biasing spring, and a head portion with laterally facing surface which frictionally engages a cooperating surface on the coupled retainer member which defines the sliding interface. The retainer member is preferably a ring-like member which surrounds at least the head portion of the needle-holding member. Since the frictional engagement force which exists at the sliding interface exceeds the retraction force provided by the compressed spring, the spring force acting on the needle-holding member forces the retainer member up against the stop member.

The transition zone in the hollow body is inwardly laterally constricted where the stop member is located, to define an internal opening into the hollow first end portion of the elongate hollow body. The head portion of the needle holder is capable of passing through the internal opening while the retainer member is larger than the internal opening. A portion of the retainer member extends laterally inwardly beyond the stop member to the sliding interface where it is coupled to the needle holding member. This exposes a generally transverse upper surface to action from above. The head portion of the movable member at the front thereof has a wall adapted to push against the exposed transverse upper surface of the retainer member when the movable member is selectively moved from a first position to a second position, the first position placing the wall of the head portion in the immediate presence of the transverse surface. The second position of the movable member is the position of the movable member upon further movement of the movable member in the forward direction until retraction occurs. The front of the head portion of the movable member or syringe plunger is sized to pass through the internal opening where the stop member or members are located, and has a hollow interior including an entrance to a hollow retraction cavity within the plunger. The entrance and the hollow cavity are larger in diameter than the head of the needle holding member, which permits the needle holding member to enter the retraction cavity after the retainer member is separated from the needle holder.

The head of the movable member or plunger has a piston below which a variable fluid chamber is defined, in the second part of the elongate hollow body above the transition zone. The hollow needle extends from the body through the closure member in fluid communication with the variable chamber to perform the usual function of a syringe. The wall of the head portion of the plunger extends forwardly ahead of the piston and contains a dislodgable plug member which seals the entrance to the retraction cavity in the movable member or plunger. The dislodgable member is dislodged, upon movement of the movable member from the first position to the second position, by contact with the needle holding member, preferably before the needle holding member is separated from the retainer member during selective movement of the movable member to effect retraction.

Thus it can be seen that the invention embodied in a syringe in the usual tubular cylindrical construction can be filled with an injection fluid in the usual manner and adjusted to remove the air bubbles and adjust the dose. When the plunger is moved forwardly, the variable fluid chamber is reduced in size and fluid is ejected through the hollow needle fixed in the center of the needle holding member. At the end of the injection stroke, the front wall or lip of the head of the plunger is positioned immediately in the presence of the retainer member in line with the retainer member without also being positioned in line with the needle holding member. This is the first position of the plunger. Further depression of the plunger in the forward direction causes the front part of the plunger to begin pressing on the retainer member and dislodging the plug member. Continued depression of the plunger begins moving the retainer member in a forward direction away from the stop members reducing the extent of the sliding interface area. The needle holder remains in its original position because it is bottomed out against the tip closure. The plug member is slidingly dislodged during gradual reduction of the sliding interface.

As the plunger continues to move forwardly from the first position toward the second position, the retainer member (ring) is shifted axially and the sliding interface is gradually reduced until finally the frictional engagement between the retainer member anti the needle holder is less than the retraction force provided by the spring, the retainer separates from the head of the needle holder and the spring drives the needle holder and needle along with the dislodgable plug member into the retraction cavity in the center of the plunger thereby effectively and permanently retracting the needle inside the hollow body. The front portion at the head of the plunger may also be equipped with hooked portions which pass through the internal opening in one direction during movement of the plunger in order to effect separation of the retainer member from the needle holder. The hooked portions engage locking means which are preferably a portion of the stop members themselves, such that the interengagement of the hooked portions with one or more locking surfaces prevents movement of the plunger in the retraction direction after retraction has occurred.

It is noted that the release mechanism does not require the use of thin, breakable sections or flexible fingers which are difficult to mass-produce and difficult to control. There are no breakable parts to float around within the syringe which may cause hang-ups. A smooth retraction force of a predetermined nature is provided by the simple frictional engagement of the retainer member on the needle holder. A slight taper or draft at the sliding interface between the needle holder and retainer ring makes it possible to essentially calibrate the friction holding force by a very slight wedging action during assembly under a predetermined load. This determines how much force transmitted by the plunger is what is required to initiate sliding separation when the retainer member is slid forwardly. This makes it easy to predetermine the amount of thumb pressure required on the plunger in order to effect retraction. The required retraction force is reproducible by assembling the two pans with the same axially applied assembly force, even if there are slight differences in diameter at the interengaging sliding interface of the retainer member and needle holder.

Another feature of the medical device in the form of a syringe is a two-position end cap which is mounted on the rear portion of the plunger and which serves to transmit the thumb pressure used to depress the plunger. In a first position of the end cap, the end cap cooperates with the hollow body by means of an engaging wall which bottoms out against a ledge in the rear portion of the body to position the plunger in the first position. No reasonable amount of forward pressure on the plunger will initiate retraction because the end cap and the body are in hard contact. When the end cap is pulled back to fill the plunger, it moves to the second position which corresponds to the second position of the plunger. There is also a locking means which locks the plunger in the second position. Now when the plunger is moved forward during the injection cycle, its movement is not limited until it reaches the second position defined as the most forward position of the plunger after retraction has taken place. The cap member cannot be returned to its first position, to help insure that the medical device cannot be reused. The two position end cap conveniently opaquely covers a colored indicia which is revealed when it is pulled back to the second position. This exposes a warning band to indicate that the syringe has been used or tampered with.

Of particular advantage is the ease of manufacture and assembly of the syringe made according to the invention. The syringe body may be formed with or without a contraction in diameter below the transition zone where the retraction mechanism is located. The plunger may have a contraction in diameter at the front opening of the hollow internal retraction cavity, but neither of these structures require collapsible core pin technology which can greatly extend cycle time in mass production. Core pins can be put in from both directions to form a first reduced diameter front portion.

The dislodgable plug member is easily installed through the open rear end of the plunger and pushed forward until a land engages a reduced diameter of the front opening or entrance portion of the head of the plunger to hold the plug member in sealing contact with the inner surfaces. The cap member is then installed at the rear to close the opening after the plug member is inserted.

The retainer member preferably has sufficient depth to provide a stabilizing. positioning and locating function with respect to the needle holder by contact with the walls of the open front end portion of the body. The combined needle holder and retainer member are slid in sealing contact with the side walls up to the transition zone, the spring inserted over the stem of the needle holder and the closure member cap fixed in place by compressing the spring. The spring is isolated from any fluid introduced into the fluid chamber above the transition zone. Assembly can be accomplished by automated mechanized means. No tip seal is required which permits a large opening which easily accommodates slight misalignment with the needle off the true central axis of the device.

The many advantages of the invention will be seen in the following detailed description.

DETAILED DESCRIPTION OF THE INVENTION

Figure 1:
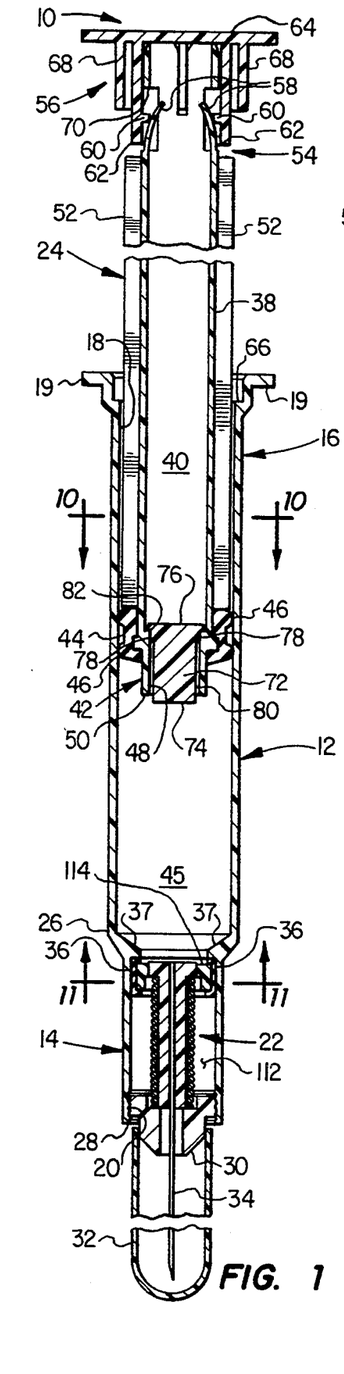
FIG. 1 is a longitudinal cross-sectional view of a first embodiment of the invention illustrating a syringe in shipping position with the plunger partially withdrawn.

In FIG. 1, a first embodiment of the invention is a syringe indicated generally by the reference numeral 10. Syringe 10 has an elongated hollow body 12 having a wall defining a hollow interior with a first end portion 14 and an opposite second end portion 16. Second end portion 16 of body 12 defines an opening 18 for an elongated plunger assembly generally designated by the numeral 24. Finger tabs 19 extend laterally from body 12. First end portion 14 of body 12 defines an opening 20 and cavity 112 for a needle assembly generally designated by the reference numeral 22.

The wall of body 12 is generally straight as it extends downward from opening 18 until reaching a transition zone 26 where it is necked in to define the first end portion 14 which is smaller in diameter than the main portion of body 12. Transition zone 26 terminates in an abutment stop 36 at the upper end of front portion 14. Abutment stop 36 may be an inwardly projecting annular wall 37 or segments of an annular wall or other suitable stop structure. The front end 28 of the first end portion 14 of body 12 has a closure member 30 mounted in opening 20. A threaded engagement is illustrated. Closure member 30 may have a conical projection suitable for holding a needle cap 32 to protect needle 34 during shipment and prior to use. Needle cap 32 has an open end which frictionally engages a cooperating surface on closure member 30 so that it is quickly and easily removed.

Elongated plunger assembly 24 has a wall 38 defining a hollow interior 40, a first end portion or head 42 and an opposite second end portion 54. First end portion 42 of plunger 24 constitutes a head of plunger assembly 24 carrying piston 44 having annular sealing surfaces 46 adapted to slide in sealed contact with the interior wall of hollow body 12. The first end portion or head 42 terminates at a lip 50 defining an opening 48. The syringe body 12, plunger assembly 24 and the openings therein are preferably circular, as shown, like a standard syringe.

Figures 9, 10, 11, 12, 13:
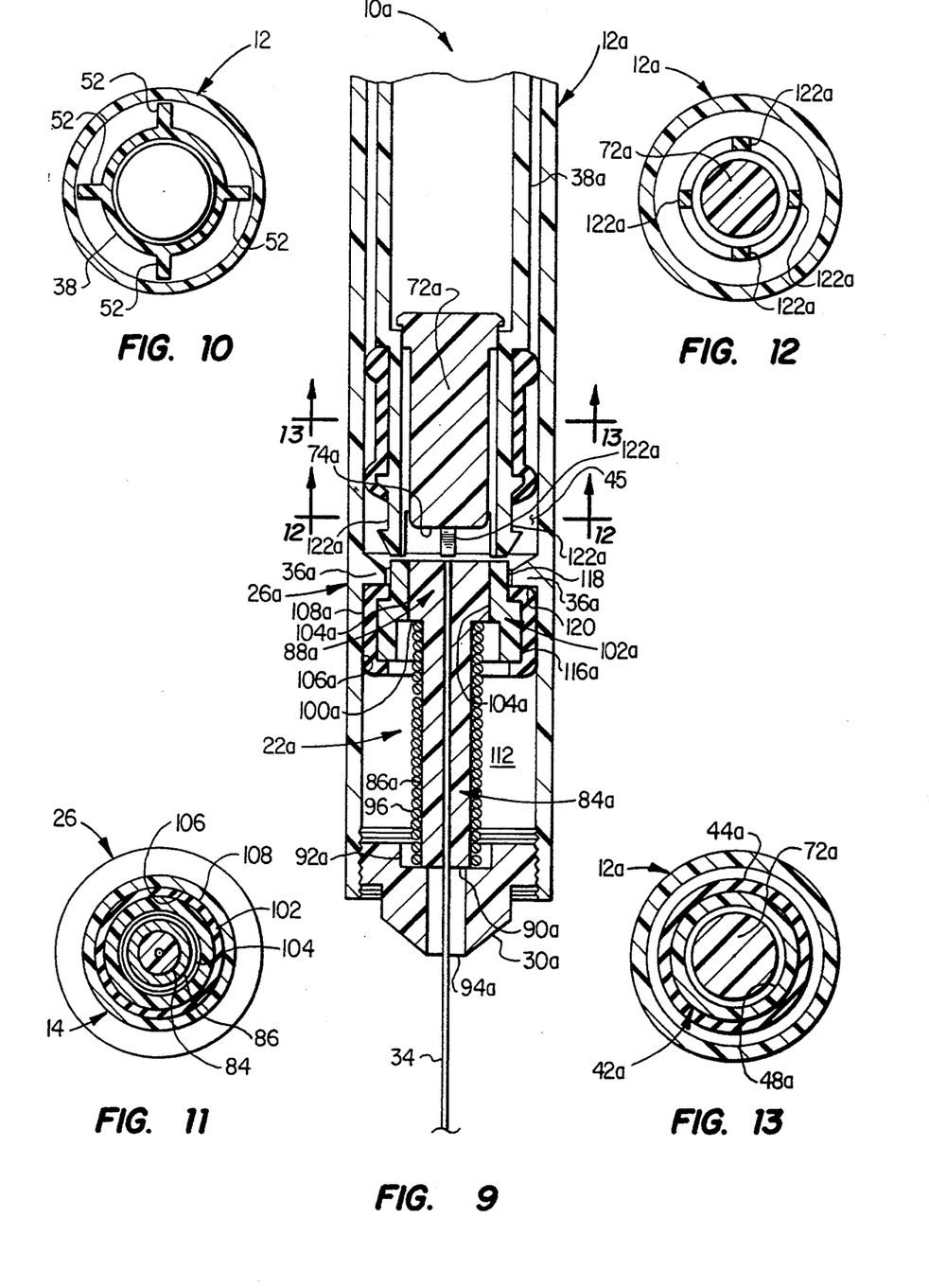
FIG. 9 is an enlarged cross-sectional view of the embodiment of FIGS. 6-8.
FIG. 10 is a cross-section on lines 10—10 of FIG. 1.
FIG. 11 is a cross-section on lines 11—11 of FIG. 1.
FIG. 12 is a cross-section on lines 12—12 of FIG. 9.
FIG. 13 is a cross-section on the lines 13—13 of FIG. 9.

Plunger wall 38 preferably has radially extending projections 52 best seen in FIG. 10. These projections extend longitudinally upwardly from the first end portion or head 42, terminating a short distance from the back end. Projections 52 serve as sliding guide members for the plunger to maintain its lateral position on the central axis of syringe body 12. At the back of the plunger, second end portion 54 is formed to include a positioning means for a two-position end cap 56 which fits over the back end of the plunger. Two to four flexible fingers 58 molded into wall 38 are surrounded by an open slot in wall 38. Fingers 58 are forced inwardly by complimentary radially inwardly extending projections 60 formed in a downwardly extending wall element 62 depending from a horizontal thumb bar 64 of end cap 56. Wall element 62 may be an annular wall with projections 60 located to cooperate with flexible fingers 58. To complete the structure, another circular wall 68 depends from thumb bar 64 of cap member 56 spaced outwardly from wall 62. An annular abutment ledge 66 formed on wall 38 serves as a stop for the end of wall 68.

The general idea of movable end cap 56 is that it provides a means for positioning plunge assembly 24 in two positions within the syringe body. When end cap 56 is in a first position represented in FIG. 1, plunger travel is limited because wall 68 bottoms out by contact with ledge 66 formed in the upper end of the syringe body. When end cap 56 is moved back to a second position represented in FIG. 3, plunger head 42 can move closer to the front of the syringe sufficiently to trip a retraction mechanism before end cap 56 bottoms out. The first and second positions of the end cap correspond to first and second positions of the plunger.

Figures 2, 3:
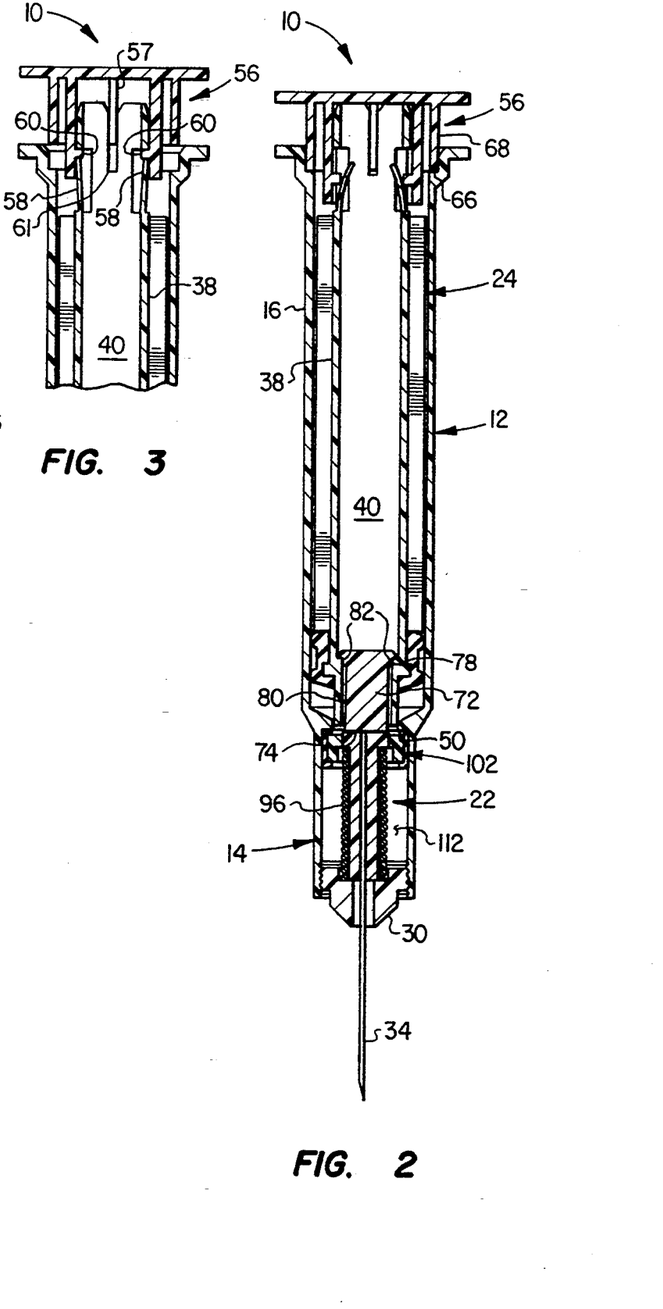
FIG. 2 is the embodiment of FIG. 1 with the plunger in the depressed position at the end of the injection cycle.
FIG. 3 shows the plunger end cap after movement from a first position to a second position in preparation for automatic retraction of the needle upon further forward movement of the plunger.

Annular wall 68 is preferably opaque to surround and hide a colored surface at the uppermost end of second end portion 54 in the first position shown in FIG. 1. A brightly covered area covered by opaque member 68 is exposed when the end cap is moved axially rearwardly to the second position with respect to end portion 54 of the plunger. When end cap 56 is pulled back with respect to the remainder of the plunger from the first position to the second position, the projections 60 lock in gaps 70 above fingers 58. In FIG. 3, fingers 58 flex outwardly to rest under projections 60 and prevent the end cap from being moved relative to the plunger. The end cap is in effect locked into the second position and cannot be returned to the first position. A longitudinally extending guide 57 and cooperating slot aligns the cap in proper position. After the syringe is used, the brightly covered band at the top of portion 54 thus becomes visible to indicate previous use.

The opening at the front of the plunger is closed by means of a dislodgable plug member. First end portion 42 contains plug member 72 having a lower end 74 extending slightly beyond lip 50 and a wider head portion 76 having a land 78 just below the head portion. The land is a smaller diameter than head portion 76, but larger in diameter than body portion 80. Land 78 sealingly engages a cooperating sealing surface 82 in the interior of plunger 24. Plug member 72 is frictionally held at cooperating sealing surface 82 within the interior in the first end portion of plunger assembly 24 and seals the opening into interior 40 at land 78. Except for a small gap between opening 48 and plug member 72, no fluid from variable fluid chamber 45 can enter interior 40 with the plug member in place.

Figure 5:
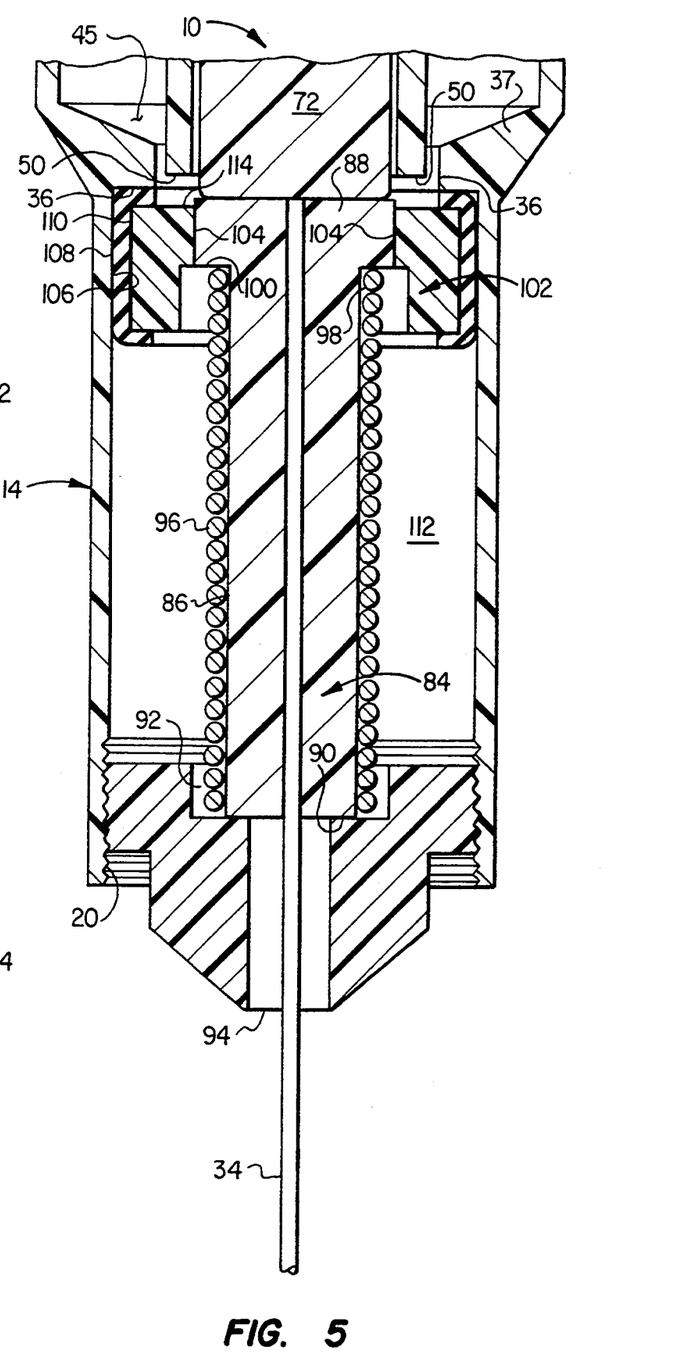
FIG. 5 shows an enlarged embodiment of FIGS. 1-4 as the front of the plunger comes into contact with the needle assembly to begin the retraction stroke.

The needle assembly 22 is best illustrated in FIG. 5 and in cross-section in FIG. 11. In FIG. 5, a hollow needle 34 is held securely by a needle holder 84 having a stem portion 86 and a head portion 88. It has a lower end 90 and is generally shaped like an elongated "T." End 90 of needle holder 84 rests in a cavity 92 of closure 30 with needle 34 extending centrally through opening 94. The opposite other end of needle 34 extends in fluid communication with variable fluid chamber 45 above head portion 88.

A compressed spring 96 surrounds stem 84. The front end of spring 96 is in contact with the bottom of cavity 92. The back end 98 presses against the underside surface 100 of head 88. The force thus produced tends to drive the needle holder into variable fluid chamber 45.

A separable retainer member or retainer ring 102 is carded by head 88 of the needle holder 84. Retainer member 102 and head 88 are assembled together with a sliding interface 104 whereby the needle holder may be selectively released by gradual reduction of the amount of sliding surface caused by axial movement of retainer member 102 relative to needle holder 84. Retainer member 102 is frictionally engaged with the head of the needle holder at the sliding interface 104.

Retainer 102 surrounds head 88 of the needle holder in sliding sealed contact with the interior wall surface 106 at the upper end of first end portion 14, either directly or with the aid of sealing member 108 mounted on the annular outer surface 110 of retainer 102. Retainer member 102, either directly or with the aid of sealing member 108, is held in contact with abutment stop 36 under the influence of the biasing element, spring 96, acting on needle holder 84. Retainer member 102 with or without sealing element 108 effectively seals any fluid in variable chamber 45 from any contact with spring 96 and from entering any part of cavity 112 in lower end portion 14. Consequently, no seal is needed at the tip of the syringe where the injection needle exits.

Assembly is exceedingly easy because needle 34 can be epoxied or otherwise fixed in needle holder 84 as indicated in FIG. 5, retainer member 102 can be frictionally engaged with head 88, spring 96 is slid over stem 86 and the whole needle assembly pushed upwardly positioned against stop 36. The closure member then holds the whole needle assembly in position. No seal is necessary at the lower end of front end portion 14.

Returning to FIG. 2, one sees plunger 24 in the first position with the end cap also in the first position. Needle 34 may be passed through a membrane into a body of injection fluid which is drawn into variable chamber 45 by pulling back on end cap 56. This preferably moves the end cap to the second position illustrated in FIG. 3. After the syringe has been filled with sufficient fluid and adjusted to remove air and excess fluid, it is ready for the injection and retraction cycle. With the injection needle in place, the plunger is depressed. All but a tiny amount of the fluid flows from chamber 45 through needle 34. At the end of the injection stroke and beginning of the retraction stroke, the piston is in the position shown in FIG. 2, except that the end cap is in the second position of FIG. 3. Now the plunger can be depressed still further beyond the first position.

As the plunger moves forward, lower end 74 of plug member 72 is in contact with the upper end surface of head 88 of the needle holder. Since the lower end 90 of needle holder 84 is bottomed against closure member 30, the needle holder can't move. Forward movement of plunger 24 dislodges plug member 72 by moving land 78 relative to sealing surface 82. This causes plug member 72 to begin moving backward within cavity 40 toward end cap 56. Simultaneously, lip or end 50 of the plunger comes in contact with transverse upper surface 114 of retainer 102. Further depression of plunger 24 causes retainer 102 to begin separating from the head of needle holder 84 by sliding axially along sliding interface 104. Lip 50 pushing against transverse surface 114 slides the retainer relative to the needle holder until the needle holder is separated from the retainer member whereby the needle holder and needle are driven into the hollow interior of the plunger under the influence of compression spring 96 driving needle holder 84. Plug member 72 is carried along into space 40.

Figure 4:
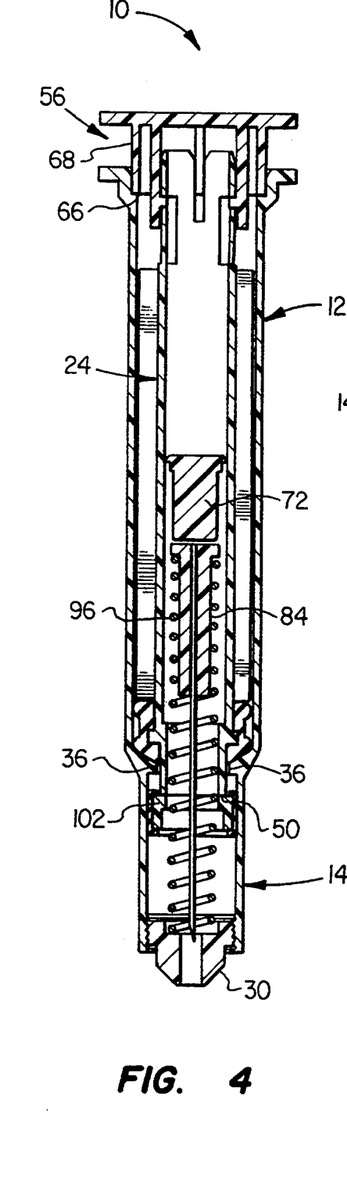
FIG. 4 shows embodiment of FIGS. 1-3 with the needle assembly retracted into the hollow interior of the plunger in response to movement of the plunger from the position of FIG. 3 to the position of FIG. 4.

FIG. 4 illustrates the retracted position of the needle holder and needle after the needle holder has moved in response to the retraction operation just discussed. It shows the position of the retainer member just after axial movement of retainer member 102 in response to depression of the plunger releases the needle holder by gradual reduction of the sliding interface between the needle holder and the retainer. Examination of FIG. 4 will indicate that further movement of the plunger in either direction can have no effect on movement of the needle. The needle holder and retainer constitute two separable parts which when separated allow the retraction to take place. Once that separation has occurred, the needle is permanently retracted into the hollow plunger. After retraction, it is difficult, if not impossible, to reassemble the syringe, even if the plunger is removed from the body, because retainer member 102 is trapped in the front end portion of the body, the end cap is permanently locked to the otherwise open end of the plunger and closure 30 is preferably permanently fixed in place.

Figure 6:
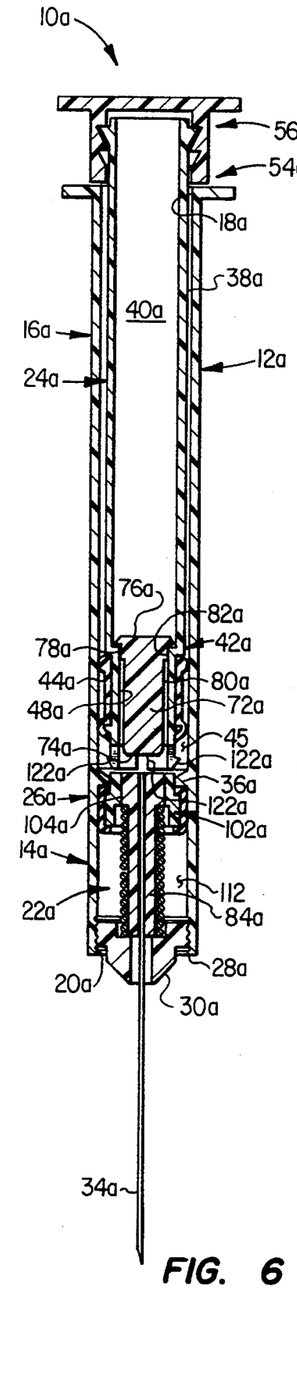
FIG. 6 is a longitudinal cross-sectional view of a second embodiment of a syringe showing the front of the plunger at the end of the injection cycle ready to contact the needle assembly to initiate retraction of the needle.

A second embodiment is shown in FIGS. 6–9 with cross-sections shown in FIGS. 12 and 13. Subscripts are used to indicate similar parts. In FIG. 6, the second embodiment is generally indicated by the reference numeral 10a. Syringe 10a has elongated syringe body 12a having a wall defining a hollow interior, a first end portion 14a and an opposite second end portion 16a. The back end of second end portion 16a defines an opening 18a for an elongated plunger assembly 24a. Cylindrical body 12a has a transition zone 26a which separates a variable chamber 45 from the first end portion 14a at the front of body 12a. The front end 28a of portion 14a defines opening 20a leading to internal cavity 112. A closure member 30a is mounted in opening 20a in support of a needle assembly generally designated by the reference numeral 22a. Transition zone 26a at the back of front portion 14a has an inwardly projecting abutment stop 36a formed in the wall at the upper end of front portion 14a.

Turning now to FIG. 9, needle assembly 22a comprises a generally "T"-shaped needle holder 84a having front end 90a in contact with a cavity 92a in closure member 30a. Needle holder 84a fixedly and centrally holds needle 34 in fluid communication with variable chamber 45. Needle holder 84a has a long stem-like body portion 86a surrounded by a biasing means comprising compression spring 96. Stem 86a has a head portion 88a formed with an under surface 100a in contact with the upper end of spring 96. The force produced by spring 96 against surface 100a tends to drive the needle holder into variable fluid chamber 45.

Needle assembly 22a is a separable two-part needle assembly. The "T"-shaped needle holder 84a being a central needle-holding part, the other part being a separable frictionally held retainer member 102a which surrounds and frictionally engages the head portion 88a at a sliding interface 104a which comprises the annular outer surface of head 88a and the inner surface of retainer member 102a. Retainer 102a extends laterally and has a slidable sealing surface in contact with syringe body wall 106a, either directly or through a sealing member 108a in contact with the outer surface 116a of retainer 102a. Retainer 102a either directly or indirectly, through the interposition of sealing member 108a, is held against a lower surface 120 of inwardly projecting stops 36a. Retainer 102a may have an upper portion 118 extending past stops 36a into the bottom of variable chamber 45. Stops 36a project radially inwardly and have the locking surface 120 against which the retainer member is held under the biasing influence of the spring acting on the central needle-holding part 84a.

Plunger assembly 24a in FIGS. 6–9 has a wall 38a defining a hollow interior 40a, first end portion 42a, which may be referred to as the head of the plunger, and an opposite second end portion 54a. Head 42a carries a piston 44a in sliding sealed contact with the wall of the hollow interior of body 12a. The head of the plunger has a reduced diameter which forms a hollow 48a with a sealing surface 82a at the upper end comprising a means for sliding sealing engagement with a land 78a formed under the head 76a of a dislodgable plug member 72a. This is like plug member 72 of the first embodiment, except having a longer body 80a and a suitable diameter to permit dislodgably sealing the head so that fluid does not enter cavity 40a.

In the case of plunger assembly 24a, head 42a has a plurality of angularly shaped hooked projections 122a also seen in FIG. 12. These are extensions beyond lower face 74a of dislodgable plug member 72a. Projections 122a are straight (arcuate) extensions of the wall of head 42a with an outwardly extending hook or barb which is designed to catch locking surface 120 under inwardly facing stops 36a when the plunger is depressed for retraction. The hooks prevent subsequent withdrawal of the plunger. Since the plunger in the second embodiment is much closer to the inside diameter of the syringe body, no guide members are needed along wall 38a. Plunger assembly 24a still includes a two-position cap member 56a which is indicated schematically in FIGS. 6–8 as a circular cap with flat bottomed angled grooves which selectively engage corresponding teeth on the outside of the upper end of the plunger. It could be the two-position cap member 56 or some other cap that selectively moves between the first and second positions to so position the plunger.

The operation of the second embodiment is best illustrated by reference to FIG. 6–8 and 9. In FIG. 6, the plunger is illustrated just at the end of the injection cycle. The distal ends of hooked projections 122a are aligned with and about to come into contact with the upper surface of retainer member 102a. The inside diameter between hooked projections 122a is such that the opening created therein cannot also come in contact with any portion of the head 88a of needle holder 84a. The plunger now moves axially in response to thumb pressure on the end cap toward the second or retraction position. The plug member 72a comes into contact with the upper surface of the head of the needle holder which is fixed in place. The plug member dislodges from sealing surface 82a by slippage of land 78a until it comes free.

Figure 7:
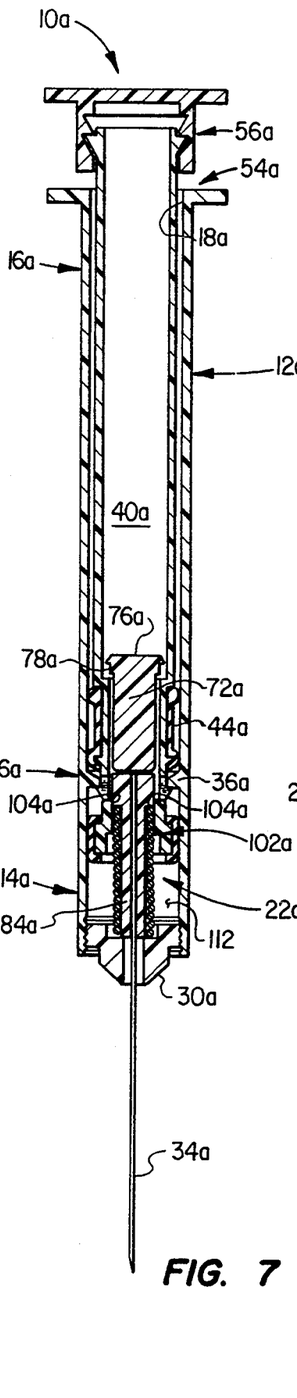
FIG. 7 is the embodiment of FIG. 6 showing the end cap of the plunger moved back to the second position allowing the retainer member to slide downwardly relative to the needle holder just before the retraction mechanism automatically fires.

As the plunger moves downward in FIG. 7, plug member 72a is dislodged and retainer 102a has slid, relative to the head of needle holder 84a, along sliding interface 104a. This illustrates some sliding of the retainer member before the plug member comes into contact for dislodgement against the head of the needle holder. It is easily seen that by adjusting the position or length of the plug member, it could be dislodged first, just as in the first embodiment. In the position shown in FIG. 7, the area of sliding interface is seen as being reduced to the point where there is a very small remaining interface for frictional engagement between the retainer member and the needle holder. The remaining frictional engagement is insufficient to resist the biasing retraction force produced against the underside 100a of the head of the needle holder by the spring member. This retraction force now exceeds the frictional retaining force, and in FIG. 8 drives the needle holder together with the needle and the plug member into the hollow cavity 40a of plunger 24a.

Figure 8:
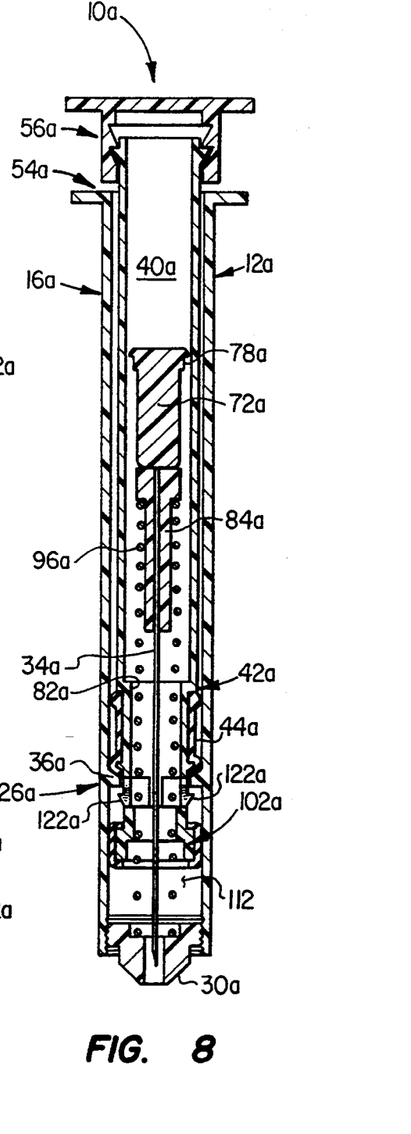
FIG. 8 shows the embodiment of FIGS. 6-7 after retraction has occurred.

In the fully extended position of the spring, the needle is completely enclosed within the syringe body and cannot be re-extended. The dimensions of the parts are adapted to cause hooked projections 122a to flex slightly inwardly by contact of the angled outwardly facing surfaces with the innermost radially extending surfaces of abutment stops 36a and there is sufficient clearance with respect to head 88a to permit inward flexing without binding against the head of the needle holder. The hooked projections preferably lock under the abutment stop just before the retraction occurs. The plunger now remains locked in place because of the interaction between hooked projections 122a and locking surfaces 120, which prevents any attempt to remove the plunger from the syringe body. Consequently, even if the end cap 56a were forced off, the plunger could not be removed to reuse the syringe.

Assembly of either the first or second embodiment is quick, easy and well-suited for mechanization. It must be recognized that modern needles when mounted in needle holders or hubs are rarely perfectly aligned and straight. Thus, any assembly which requires passing the needles through a small opening are doomed to failure because the extremely sharp tip will catch the side and jam the equipment. Since the invention requires no seal at the tip, it is possible to provide a large opening in closure member 30a which is limited only by the requirement that it be able to support the bottom of the needle holder.

The head of the needle holder and the inside diameter of the retainer member are frictionally engaged and slid into the open end of front portion 14a. By contact with the inner wall of the cavity 112, the retainer member self-aligns the needle holder and needle on the central axis of the syringe. Self-alignment is provided by depending portions of the retainer which extend below the head of the needle holder. They are not essential. The spring is then placed on the stem portion of the needle holder and the tip closure goes on last. The needle is accessible from the side to hold the needle while the closure tip is put on.

The plunger member may be assembled as a unit and then simply inserted into the opening 18,18a. Plug member 72,72a is inserted through the opening in the back of the plunger and is easily sealingly engaged in position by application of a force from that direction. Then cap member 56,56a is installed to close the back end of the plunger and provide for the two-position operation. It may be necessary to provide a means for spreading the downwardly depending portions of the cap member in order to get it started on the end of the plunger. Longitudinal separations in the wall may be provided for that purpose. Both embodiments are assembled in the same general way.

In the best mode, the parts are circularly shaped as indicated in the cross-sections, although the invention contemplates any polygonal cross-section could be used. The pans are preferably injection-molded from suitable plastic, except for piston 44,44a, seal member 108,108a and the metal spring. The piston is suitably a rubber compound. The plug member is preferably plastic, also, but could be molded from a suitable rubber compound, as well.

The invention is well-suited for production in a 3 cc delivery size with the diameter and length selected to provide the appropriate interval spacing for marks on the body to determine dosages. No seal is required at the front of the syringe. The front tip is preferably sonically welded to prevent disassembly for reuse. The tip can also be flat instead of conical.

The syringe does not require a different barrel length to accommodate needles of different length. The length of the needle holder and spring are selected to retract a sufficient distance to accommodate the longest needle. The design is such that any shorter desired needle length will be retracted, as well.

The retainer member or ring could be a hard rubber or a tight-fitting plastic, but is preferably the same material as the needle holder. If used without the seal member, the retainer ring is larger so that it seals against the inner walls of chamber 112. Use of the same material reduces the chance of differential expansion and contraction of the retainer member with respect to the needle holder and syringe body over a wide range of temperature. A prototype without the seal member has been "fired" successfully immediately after removal from a freezer at 24° F. and an oven at 150° F. Retraction which may be regarded as "firing" or being fired occurs automatically when the plunger is pushed down or depressed into the second position.

The head of the plunger in the second embodiment is designed to lock just before the retraction is triggered by removal of the sliding retainer ring. This assures locking will occur. If the retraction is triggered first, there is a tendency to immediately stop pushing on the plunger which might not be quite locked by engagement of the hooked fingers and the stop.

The close-fitting frictional engagement between the retainer member and the head of the needle holder is such that a leak-proof seal is provided which separates the spring from the variable fluid chamber. The inner wall of chamber 112 where the retainer member is in sliding contact with the wall, or alternately a seal member surrounding the outer surface of the retainer member, is sealed. This effectively prevents any fluid from entering chamber 112, including during the retraction itself because a sliding interface maintains the seal until the very moment when the driving force of the springs separates the needle holder from the retainer member.

The design uniquely provides a means for predetermining the amount of thumb pressure force required to initiate retraction. The outer wall of head 88,88a and the corresponding inner wall of the retainer member which form the sliding interface 104,104a are preferably tapered slightly so that the sliding interface 104,104a is slightly tapered inwardly toward the front or tip of the syringe. The retainer member is preferably assembled to the needle holder before installing the combination in the front portion of the syringe body. This makes it possible to preload the combining parts under a predetermined and consistent load. For example, if the pans are combined under a force of two pounds, then it will require approximately the same two pounds to initiate separation of them. If it is desired to require a greater separation force, they can be assembled with a greater force. This also tends to obviate any slight differences in diameter of the combining parts since some axial misalignment of the retainer member with respect to the needle holder is not critical. Because the needle holder is loaded by the spring, the retainer member is always held against the abutment stops, no matter where it is positioned on the head of the needle holder. The only difference is the needle holding member may extend slightly more or slightly less into the variable chamber. Adjustable positioning of the closure member assures that the needle holder is securely held. This arrangement makes possible a wide range of initiating retraction force to suit any desired operating condition.

It is also contemplated that the plunger could have a single position end cap instead of a two position end cap. The pressure required to complete the injection cycle by force applied to depress the plunger is not normally very great. If it requires, for example, a force of one or two pounds on the plunger to cause retraction, it is relatively easy for the user to determine when the front end of the plunger hits the retainer member to complete delivery of the dose. Then a substantially greater force on the plunger will cause the retraction that effectively and permanently prevents reuse. Inspection of the syringe through the clear walls of the device clearly shows the dislodged plug member and needle holder in the plunger which signifies the fact that retraction has been implemented.

I claim:

1. In a medical device having a retraction mechanism with a needle for injecting or collecting fluid, an elongate hollow body containing a retraction mechanism and a movable member, slidable axially in the body, the retraction mechanism including a needle holding member having an unretracted position wherein the needle is extended from the body while being biased toward a retracted position entirely within the body, a biasing element for applying retraction force to the needle holding member in a retraction direction, and a release element capable of holding the needle holding member against the retraction force provided by the biasing element, the release element being triggered to release the needle holding member for retraction of the needle in response to selective movement of the movable member, the improvement comprising:

the needle holding member and release element are separable members coupled, along a sliding interface oriented in the direction of retraction, with a friction force which exceeds the retraction force;

retraction is initiated by relative sliding movement between the needle holding member and the release element, caused by selective movement of said movable member; and retraction occurs by reduction of the extent of said sliding interface in response to said relative sliding movement, until retraction force exceeds said friction force, whereby said needle holding member separates from said release element and moves into said retracted position.

2. The medical device of claim 1 characterized in that said elongate hollow body has a hollow first end portion separated by a transition zone from a hollow second end portion wherein substantially all of the retraction mechanism is located within said first end portion of the body below the transition zone.

3. The medical device of claim 2 characterized in that said transition zone includes a stop member against which the release element is positioned, prior to retraction, by retraction force from the biasing element applied to the needle holding member, said release element comprising a retainer member surrounding a portion of said needle holding member.

4. The medical device of claim 3 characterized in that the combined needle holding member and retainer member slidingly seal said first end portion from said second end portion below said transition zone, in a manner that prevents fluid introduced above the transition zone from contacting the biasing element.

5. The medical device of claim 4 characterized in that the needle holding member has a head portion and a stem portion, said stem portion serving as a guide for a biasing element which comprises a spring, said head portion having a laterally facing surface which frictionally engages the coupled retainer member and defines said sliding interface.

6. The medical device of claim 5 characterized in that the stem portion of the needle holding member is supported by a tip closure member through which said needle member is extended and retracted.

7. The medical device of claim 3 characterized in that said elongate hollow body is defined by a longitudinally extending wall which at the transition zone is inwardly laterally constricted by the presence of said stop member to define an internal opening into the hollow first end portion of the elongate hollow body, said release element is a retainer member surrounding and centrally positioning said needle holding member and said movable member has a head portion at the front thereof capable of passing through said internal opening in order to push against said retainer member without also pushing against said needle holding member to effect retraction.

8. The medical device of claim 7 characterized in that said retainer member is larger than said internal opening and said needle holding member is smaller than said internal opening such that a portion of said retainer member extends laterally inwardly, below said stop member, to the sliding interface where it is coupled to the needle member, to expose a generally transverse surface, the head portion of the movable member having a wall adapted to push against said transverse surface when the movable member is selectively moved from a first position to a second position, wherein the first position places said wall of the head portion in the immediate presence of said transverse surface and the second position is the position of the movable member after retraction occurs.

9. The medical device of claim 8 characterized in that the wall of said head portion of the movable member is equipped with hooked portions which pass through said internal opening in one direction during movement of the movable member in order to effect separation of the retainer member from the needle holding member, but which engage locking surfaces which prevent movement of said movable member in the opposite direction.

10. The medical device of claim 8 characterized in that said biasing element is in direct contact with the needle holding member without also contacting the retainer member, to apply said retraction force to the needle holding member in order to retract the needle and needle holding member when the retainer member is separated therefrom.

11. The medical device of claim 10 characterized in that the wall of the head portion of the movable member defines an entrance to a hollow retraction cavity, said entrance being sealed with a dislodgable plug member which is dislodged upon movement of the movable member from the first position to the second position.

12. The medical device of claim 11 characterized in that the dislodgable plug member is dislodged by contact with the needle holding member, before the needle holding member is separated from the retainer member, during selective movement of the movable member to effect retraction.

13. The medical device of claim 12 characterized in that the movable member has a rear portion having a two position end cap, having first and second positions that correspond with the first and second positions of the movable member, which cooperates with the elongate hollow body to selectively position the movable member in said positions.

14. The medical device of claim 1 characterized in that said movable member has a front portion and a rear portion, the movable member being selectively movable to position the front portion in line with said release element without also being positioned in line with said needle holding member in order to effect reduction of the extent of said sliding interface upon further movement of the release element without further movement of the needle holding member.

15. The medical device of claim 14 characterized in that the movable member has a means for selective positioning the movable member in a first position and a second position, said first position placing the front portion of the movable member in the immediate presence of said release element where it is capable of initiating said relative movement or said release element upon further movement, said second position being a sufficient distance beyond said first position to cause sliding separation of said release element from said needle holding member to allow retraction to take place.

16. The medical device of claim 15 characterized in that the means for selective positioning of the movable member is a two position cap member mounted at said rear portion of the movable member.

17. The medical device of claim 16 characterized in that the two position cap member has a first position corresponding to the first position of the movable member and a second position corresponding to the second position of the movable member,
the cap member being equipped with limiting means for stopping forward movement of the movable member beyond the first position when the cap member is in the first position.

18. The medical device of claim 17 characterized in that the cap member has a locking means which locks the cap member to the movable member when the cap member is moved to the second position and prevents the cap member being returned to its first position to help ensure that the medical device cannot be reused.

19. The medical device of claim 18 further characterized in that said elongate hollow body is a syringe body, said movable member is a syringe plunger adapted to slide within the syringe body rearwardly for filling and forwardly for ejecting injection fluid, wherein said cap member is movable from the first position to the second position by sliding rearwardly with respect to said plunger and thereafter to allow full depression of the plunger sufficient to effect retraction of the needle.

20. The medical device of claim 14 characterized in that the syringe body includes transition zone having a locking means inside the syringe body and the syringe plunger has a front end having one or more hooked projections which permanently engage said locking means when said plunger is moved to the second position to effect retraction of the needle.

21. The medical device of claim 15 characterized in that said front portion of the movable member has a hollow chamber equipped with a dislodgable plug member which is dislodged by contact with said needle holding member upon movement of the movable member from said first position to said second position, to permit retraction of the needle within said hollow chamber.

22. The medical device of claim 21 characterized in that the hollow chamber has an open entrance at the front portion of the movable member, occupied by the dislodgable plug member but separate therefrom, the plug member having a body being positioned within said open entrance by means of a slidable land extending between a rear part of the plug member body and a rear portion of the open entrance to said chamber whereby said plug member is dislodged by sliding of the plug member at said land in response to contact between the body of the plug member and the needle holding member during said movement of the movable member.

23. In a nonreusable syringe for dispensing fluid medication, a hollow syringe body having a front portion for receiving a needle assembly and a rear portion for receiving a plunger, a plunger disposed partially within the syringe body, having a head and with a piston means in sliding sealed contact with the interior of the syringe body and defining a variable fluid chamber below the piston, the needle assembly having a needle holder releasably mounted within said front portion having a needle fixed therein, with one end of the needle in fluid communication with said chamber and extending from the syringe body in use position, a biasing element which acts to bias the needle holder inwardly of the front portion of the syringe body, and a release element which can selectively release the needle holder to allow retraction of the needle within the syringe body in response to the action of the biasing element, the improvement comprising:
the release element is a retainer member surrounding the needle holder and serving to hold the needle holder against the biasing influence of said biasing element acting on the needle holder with the needle extended from the syringe for use:
said retainer member and the needle holder are assembled with a sliding interface between them;
the needle holder is selectively released by gradual reduction of the sliding interface caused by sliding axial movement of the retainer member relative to the stationary needle holder in response to depression of the plunger.

24. The nonreusable syringe of claim 23 characterized in that the syringe body is defined by an elongated wall having a transition zone which separates said front portion from said rear portion, said combined needle holder and retainer member slidingly sealing said front portion from said rear portion below said transition zone, in a manner that prevents fluid introduced above the transition zone from contacting the biasing element.

25. The nonreusable syringe of claim 24 characterized in that said transition zone includes a stop member against which the retainer member is positioned, prior to retraction, said retainer member surrounding a portion of said needle holder by means of frictional engagement at said sliding interface which exceeds a retraction force applied to the needle holder by the biasing element.

26. The nonreusable syringe of claim 25 characterized in that the head portion of the plunger having a lip defining an entrance to a retraction cavity within, said plunger being selectively movable to position said lip in line with the retainer member without also being positioned in line with the needle holding member in order to effect reduction of the extent of said sliding interface upon further movement of the retainer member without further movement of the needle holder.

27. The nonreusable syringe of claim 26 characterized in that the plug member slidingly seals the entrance to the retraction cavity, the plug member being slidingly dislodged therefrom during gradual reduction of the sliding interface between the needle holder and retainer member caused by axial movement of the retainer member in response to depression of the plunger.

28. The nonreusable syringe of claim 26 characterized in that the transition zone is inwardly laterally constricted by the presence of said stop member to define an internal opening into the front portion of the hollow syringe body;

said lip at the front of the head of the plunger being capable of passing through said internal opening in order to push against said retainer member without also pushing against said needle holder to effect retraction.

29. The nonreusable syringe of claim 28 characterized in that said plug member is slidingly dislodged by contact with the needle holder caused by depression of the plunger, during gradual reduction of the sliding interface which is frictionally engaging the coupled retainer member and needle holder.

30. The nonreusable syringe of claim 29 characterized in that the lip on the head is the forward extension of a wall defining said entrance, said wall being equipped with hooked portions which pass through said internal opening in one direction during movement of the plunger in order to effect separation of the retainer member from the needle holder, the hooked portions engaging locking surfaces which prevent movement of the plunger in the opposite direction.

31. In a nonreusable syringe for dispensing fluid medication, comprising a syringe body having a hollow interior and opposite open front and back ends, a needle mounted extending from a front end of the body and communicating with a variable fluid chamber defined by a plunger extending from an open back end of the syringe body and having a head sliding in sealed contact with the interior of the syringe body, the plunger movement serving to fill the variable fluid chamber of the hollow syringe body by drawing fluid from a source through the needle and to deliver fluid out of the needle after filling, where movement of the plunger at the end of the delivery movement toward the front end of the syringe body thereby triggers a retraction mechanism to retract the needle within the syringe body, the improvement comprising:

mounting the needle in a separable two part needle assembly at the front of the syringe body, one pan being a central needle holding part biased inwardly by a spring mounted forwardly of a portion of the central needle holding part, the other part being a separable frictionally held retainer surrounding and frictionally engaging a portion of the first part, said retainer extending laterally and having a slidable sealing surface in contact with the syringe body and being held against a stop positioned around the hollow interior of the syringe body which does not also contact said one part;

the plunger having a hollow interior and a lip on the plunger head which is positioned to encounter said retainer at the end of the delivery stroke without also encountering said one part; and wherein movement of the plunger slides the retainer part with respect to the central needle holding part thereby reducing the frictional engagement between said two parts until the biasing force applied to the central needle holding part exceeds the frictional holding force to cause separation of said separable pans whereby the needle is permanently retracted into the hollow plunger.

32. A nonreusable syringe for dispensing fluid medication, comprising:

an elongated syringe body having a wall defining a hollow interior with openings at opposite ends of the body, comprising a first end having an opening for receiving a needle assembly and a second end having a plunger opening for receiving a plunger assembly;

an elongated plunger assembly having a wall defining a hollow interior, comprising a first end portion having an opening, carrying a sealing surface adapted to slide in sealed contact with the wall of the hollow interior of the syringe body defining a variable fluid chamber below the sealing surface, and an opposite second end designed to extend from the plunger opening of the syringe body;

a needle assembly positioned below a stop located at the wall of the syringe body within the needle assembly opening at the first end of the syringe body, including:

a needle holder;

a needle held by the needle holder in fluid communication with the variable fluid chamber;

a biasing element acting on the needle holder tending to drive the needle holder into the variable fluid chamber; and a separable retainer member carried by the needle holder, positioned against said stop, said retainer extending laterally from said needle holder in slidable sealed contact with the wall of the syringe body to seal off the variable fluid chamber;

wherein selective movement of the plunger positions a portion of the wall defining the opening at the first end of the plunger assembly against the separable retainer member of the needle assembly and slides said retainer relative to the needle holder until the needle holder is separated from the retainer member whereby the needle holder and needle are driven into the hollow interior of the plunger away from the open first end of the syringe body, which cannot thereafter be reused.

33. In a medical device having a retraction mechanism with a needle for injecting or collecting fluid, an elongate hollow body containing a retraction mechanism and a movable member slidable axially in the body, the retraction mechanism including a needle holding member having an unretracted position wherein the needle is extended from the body while being biased toward a retracted position entirely within the body, a biasing element for applying retraction force to the needle holding member in a retraction direction, and a release element capable of holding the needle holding member against the retraction force provided by the biasing dement, the release element being triggered to release the needle holding member for retraction of the needle in response to selective movement of the movable member, the improvement comprising:

said elongate hollow body has a hollow first end portion separated from a hollow second end portion by a transition zone wherein substantially all of the retraction mechanism is located within said first end portion below the transition zone;

the needle holding member and a release element comprising a retainer member surrounding a portion of the needle holding member are separable members coupled along a sliding interface oriented in the direction of retraction, with a friction force which exceeds the retraction force;

said transition zone including a stop against which said retainer member is positioned, prior to retraction, by said retraction force;

retraction is initialed by relative movement between the needle holding member and the retainer member, caused by selective movement of said movable member; and retraction occurs by reduction of the extent of said sliding interface in response to said relative movement, until retraction force exceeds said friction force, whereby said needle holding member separates from said retainer member and moves into said retracted position.

* * * * *

UNITED STATES PATENT AND TRADEMARK OFFICE
CERTIFICATE OF CORRECTION

PATENT NO.  : 5,385,551
DATED       : January 31, 1995
INVENTOR(S) : Thomas J. Shaw It is certified that error appears in the above-indentified patent and that said Letters Patent is hereby corrected as shown below:

```
Col. 19, line 54, delete "pan" and insert --part--.
Col. 20, line 7, delete "pans" and insert --parts--.
Col. 20, line 62, delete "dement" and insert --element--.
Col. 22, line 1, delete "initialed" and insert --initiated--.
```

Signed and Sealed this

Ninth Day of May, 1995

Attest:

BRUCE LEHMAN

*Attesting Officer*   *Commissioner of Patents and Trademarks*